United States Patent
Bessho

(10) Patent No.: US 10,327,928 B2
(45) Date of Patent: Jun. 25, 2019

(54) OPERATING HANDLE AND STENT DELIVERY SYSTEM

(71) Applicant: KANEKA CORPORATION, Osaka-shi, Osaka (JP)

(72) Inventor: Sadao Bessho, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 186 days.

(21) Appl. No.: 15/490,213

(22) Filed: Apr. 18, 2017

(65) Prior Publication Data

US 2017/0216063 A1    Aug. 3, 2017

Related U.S. Application Data

(63) Continuation-in-part of application No. PCT/JP2015/071372, filed on Jul. 28, 2015.

(30) Foreign Application Priority Data

Oct. 23, 2014   (JP) ................. 2014-215947

(51) Int. Cl.
*A61F 2/82* (2013.01)
*A61F 2/95* (2013.01)
(Continued)

(52) U.S. Cl.
CPC .................. *A61F 2/95* (2013.01); *A61F 2/82* (2013.01); *A61F 2/966* (2013.01);
(Continued)

(58) Field of Classification Search
CPC .... A61F 2/966; A61F 2002/9517; A61F 2/82; A61F 2/95; A61F 2002/9505;
(Continued)

(56) References Cited

U.S. PATENT DOCUMENTS

| | | |
|---|---|---|
| 2003/0191516 A1 | 10/2003 | Weldon et al. |
| 2005/0060016 A1 | 3/2005 | Wu et al. |

(Continued)

FOREIGN PATENT DOCUMENTS

| | | |
|---|---|---|
| JP | 2005-521514 A | 7/2005 |
| JP | 2007-504897 A | 3/2007 |

(Continued)

OTHER PUBLICATIONS

An instruction manual of "Epic Biliary Stent" (medical device approval No. 22200BZX00794000), Boston Scientific Japan K. K., revised on Mar. 18, 2014 (3rd Edition). (http://www.bostonscientific.jp/templatedata/imports/collateral/Endoscopy/dfu_Epic_en.pdf).

*Primary Examiner* — George J Ulsh
(74) *Attorney, Agent, or Firm* — Birch, Stewart, Kolasch & Birch, LLP

(57) ABSTRACT

Provided is an operation handle capable of shortening an entire length and enhancing operability. The slide mechanism (S) comprises a rotating body (4) that rotates in conjunction with a rotation of the thumbwheel (3) as the rotating wheel and a slide body (5) that engages with the rotating body (4), slides. The slide body (5) is configured by a $1^{st}$ divided body (6) formed with a $1^{st}$ engaging part (6A) engaged with the rotating body (4) in the initial state, and a $2^{nd}$ divided body (7) formed with a $2^{nd}$ engaging part (7A) engaged with the rotating body (4) in the initial state and not engaged with the rotating body (4) in the position where the rotating body (4) and the $1^{st}$ engaging part (6A) is not engaged with each other. A power transmitting means (T) that transmits a driving force of the $1^{st}$ divided body (6) to the $2^{nd}$ divided body (7), to integrally slide the $1^{st}$ divided body (6) and the $2^{nd}$ divided body (7), is provided. When the engagement between the rotating body (4) and the $1^{st}$ engaging part (6A) is not engaged and the $1^{st}$ divided body (Continued)

(6) is stopped, the rotating body (4) is engaged with the $2^{nd}$ engaging part (7A) and the $2^{nd}$ divided body (7) slides to the proximal side (A).

11 Claims, 12 Drawing Sheets

(51) Int. Cl.
    *A61F 2/966*     (2013.01)
    *A61M 25/01*     (2006.01)

(52) U.S. Cl.
    CPC ............. *A61F 2002/9505* (2013.01); *A61F 2002/9517* (2013.01); *A61M 25/0113* (2013.01)

(58) Field of Classification Search
    CPC ........ A61F 2/2436; A61F 2/2427; A61F 2/24; A61M 25/0113
    See application file for complete search history.

(56) References Cited

U.S. PATENT DOCUMENTS

| | | |
|---|---|---|
| 2005/0090890 A1 | 4/2005 | Wu et al. |
| 2007/0055342 A1 | 3/2007 | Wu et al. |
| 2007/0100429 A1 | 5/2007 | Wu et al. |
| 2007/0112409 A1 | 5/2007 | Wu et al. |
| 2009/0099641 A1 | 4/2009 | Wu et al. |
| 2010/0145431 A1 | 6/2010 | Wu et al. |
| 2013/0144209 A1 | 6/2013 | Ryan |
| 2014/0324151 A1 | 10/2014 | Yamashita |
| 2016/0135975 A1 | 5/2016 | Shimoyama |

FOREIGN PATENT DOCUMENTS

| | | |
|---|---|---|
| JP | 2012-170469 A | 9/2012 |
| JP | 2013-146497 A | 8/2013 |
| JP | 2013-192566 A | 9/2013 |
| JP | 2013-536016 A | 9/2013 |
| WO | WO 2013/125332 A1 | 8/2013 |
| WO | WO 2015/012007 A1 | 1/2015 |

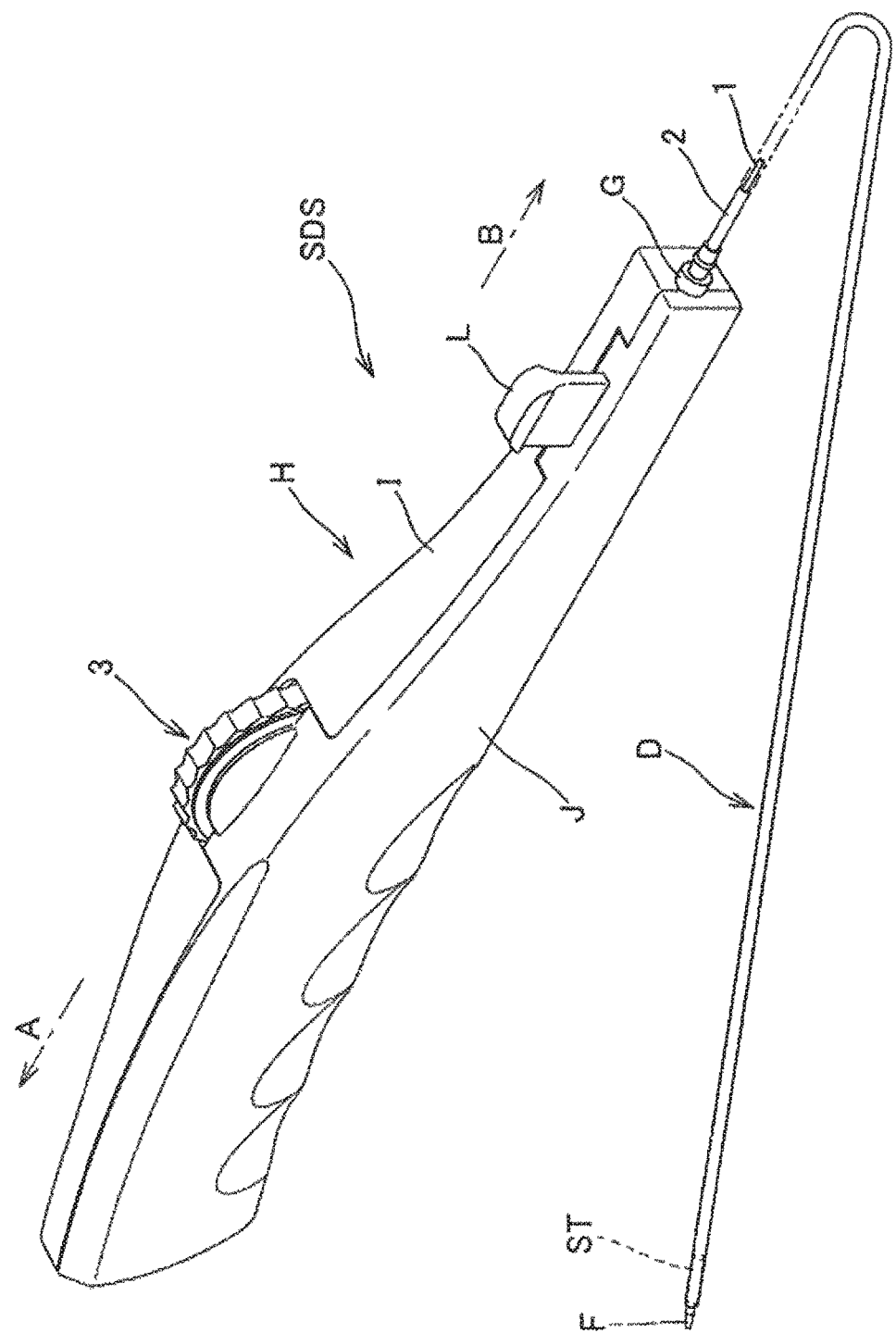
[Fig. 1]

[Fig. 2A]
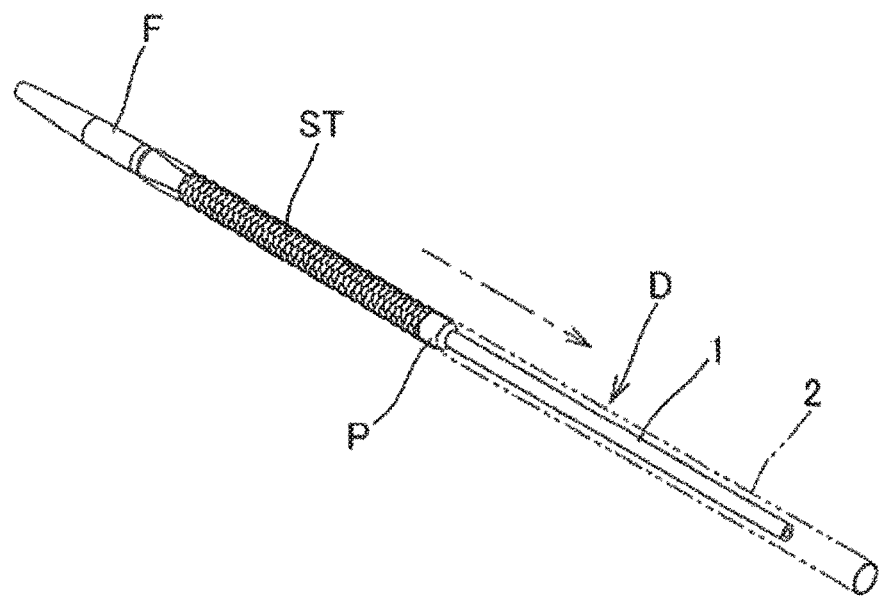
[Fig. 2B]
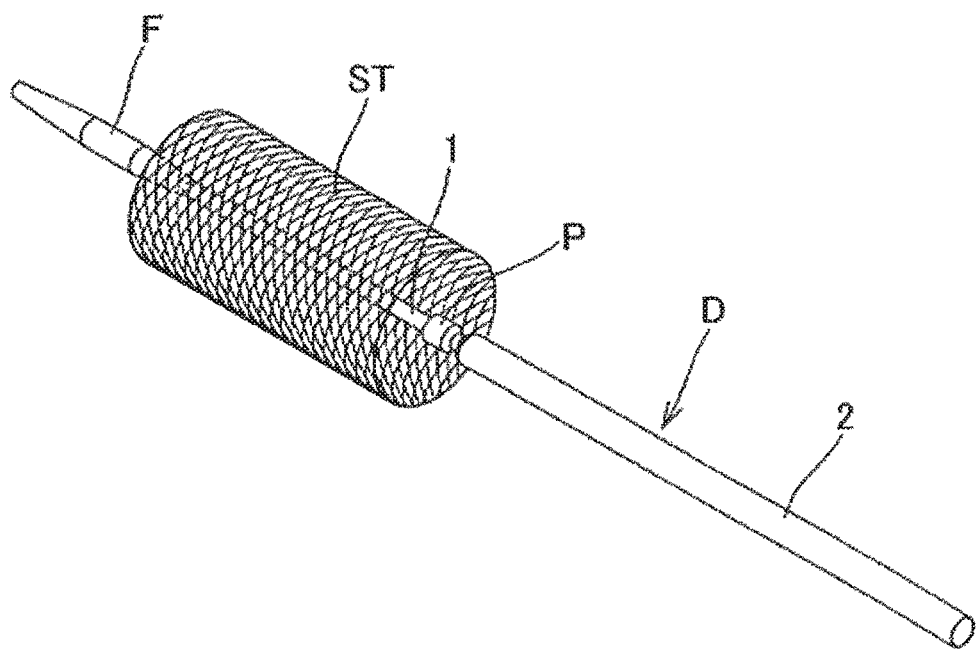

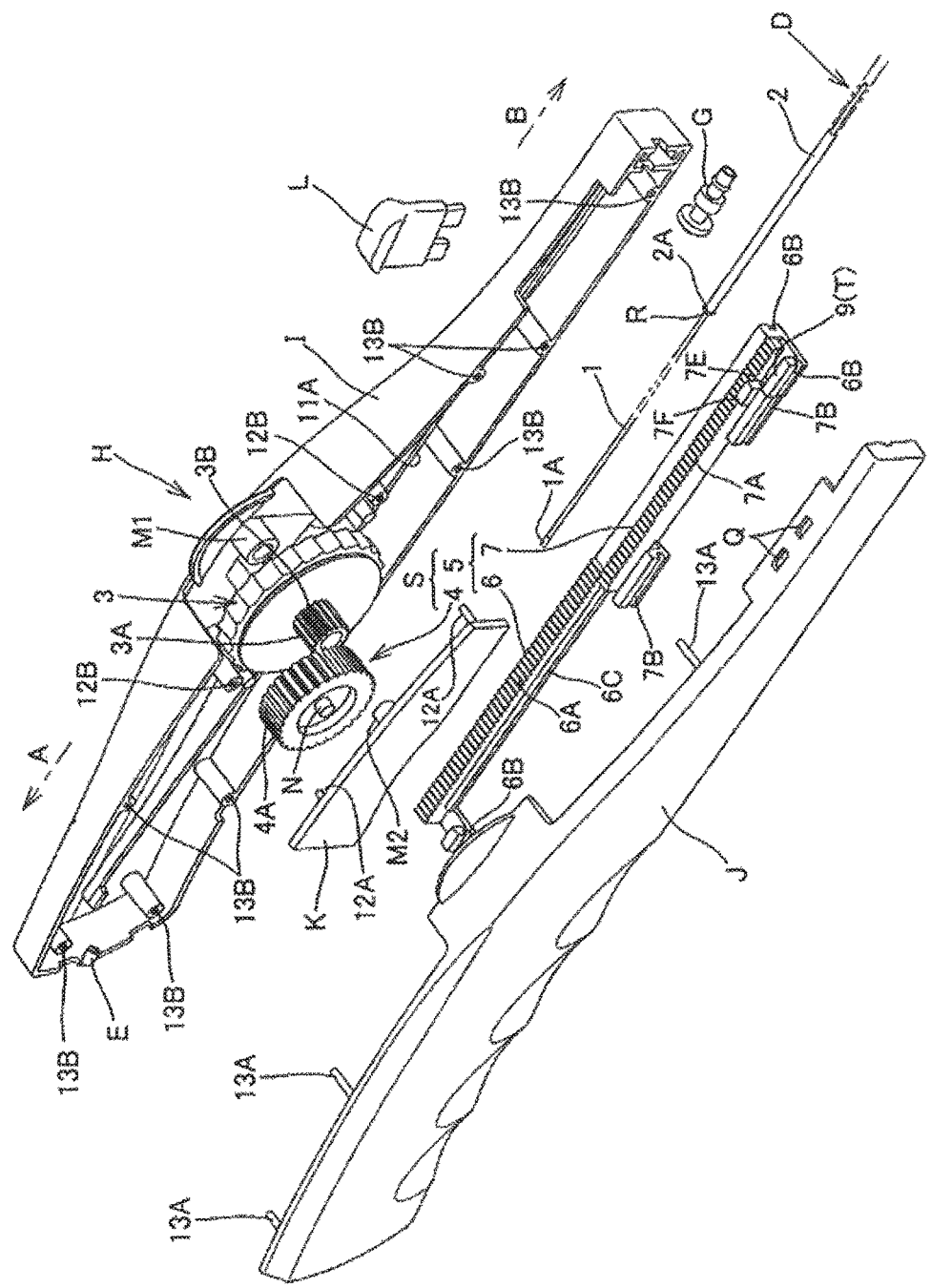
[Fig. 3]

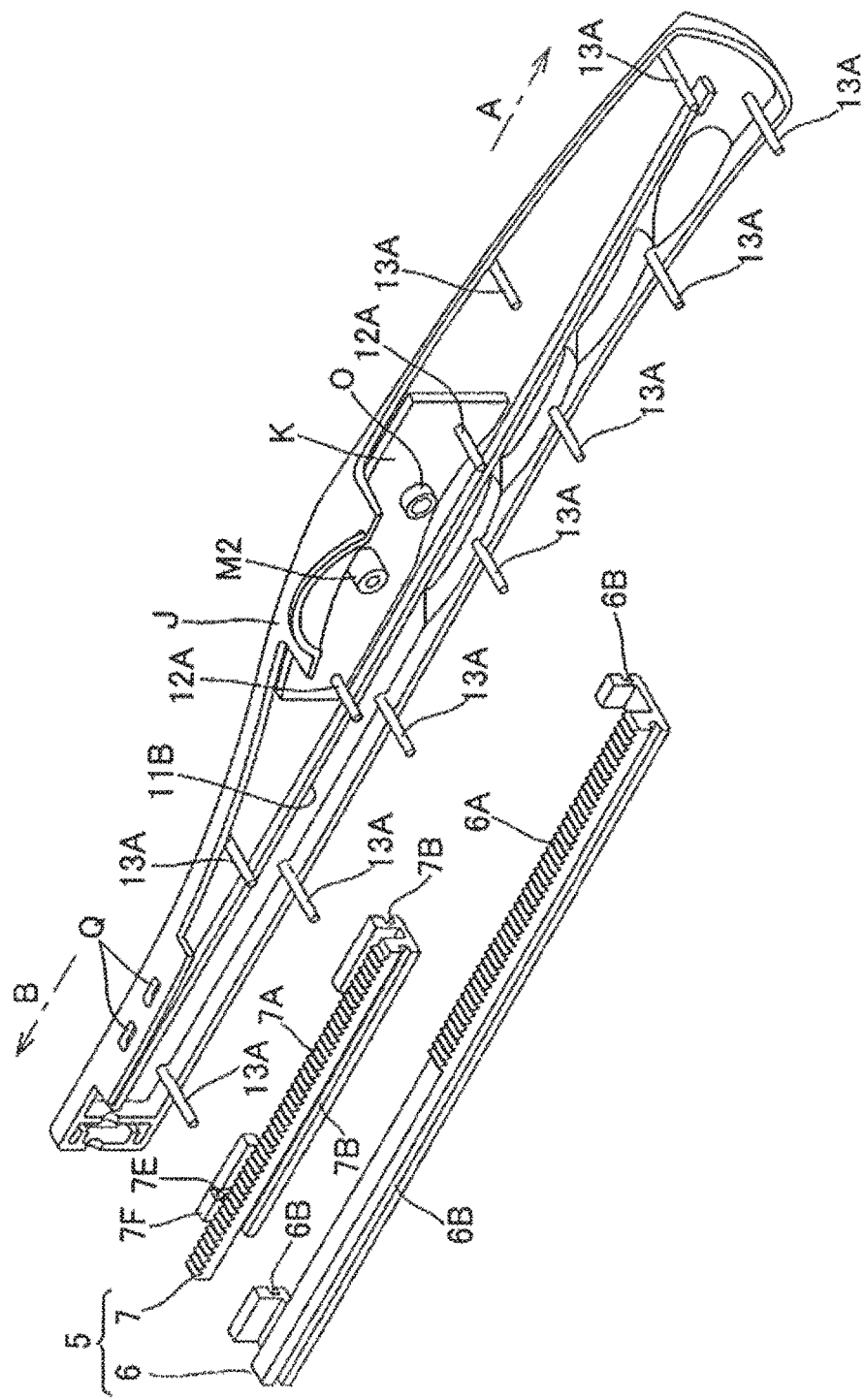
[Fig. 4]

[Fig. 5A]
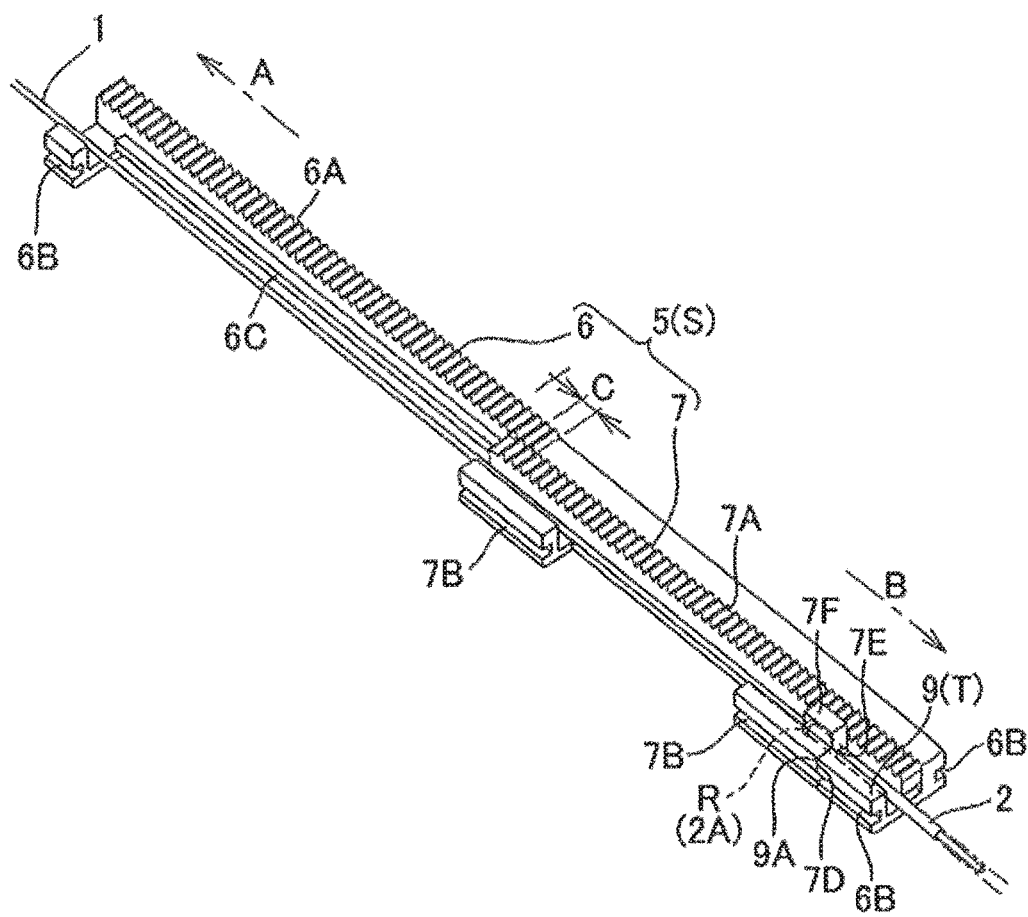

[Fig. 5B]
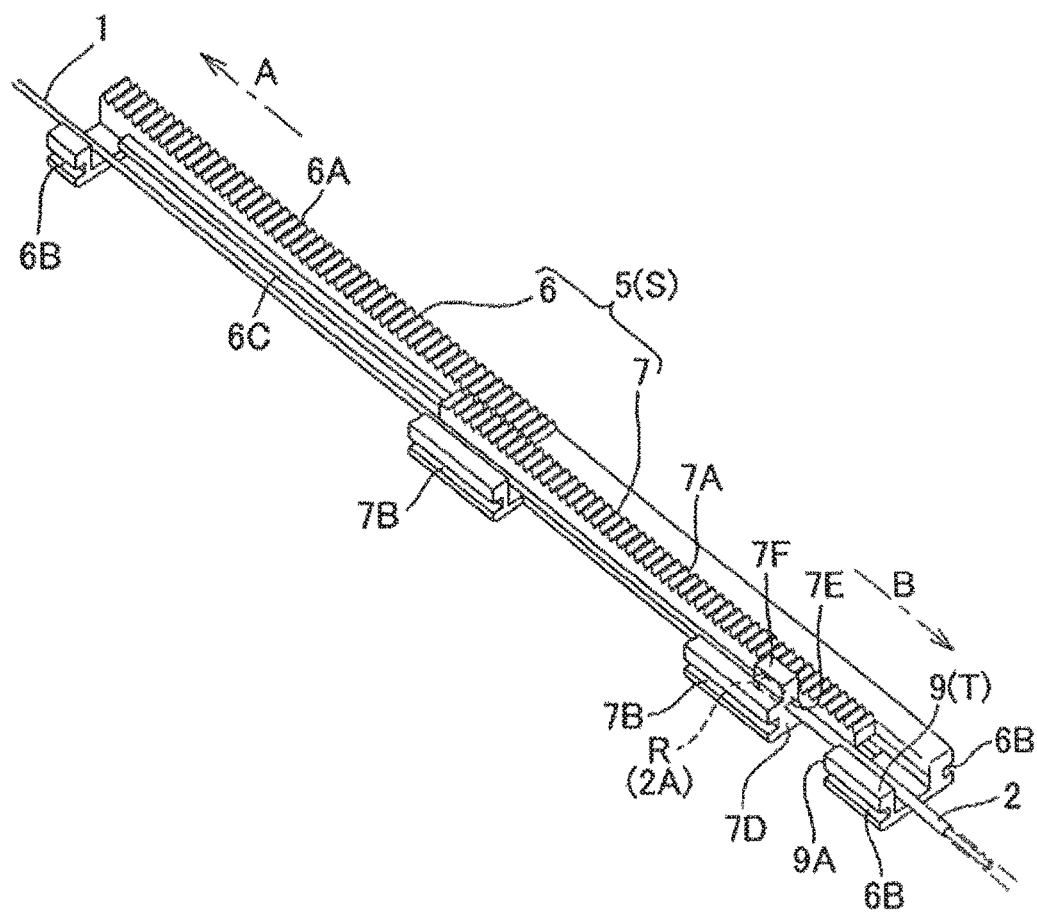

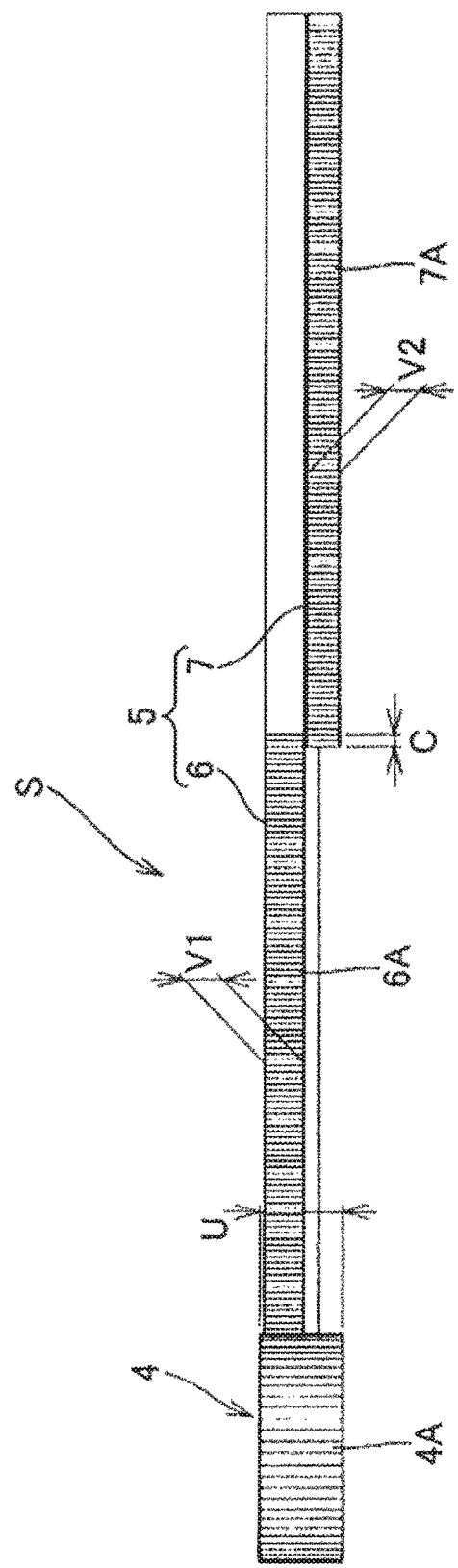

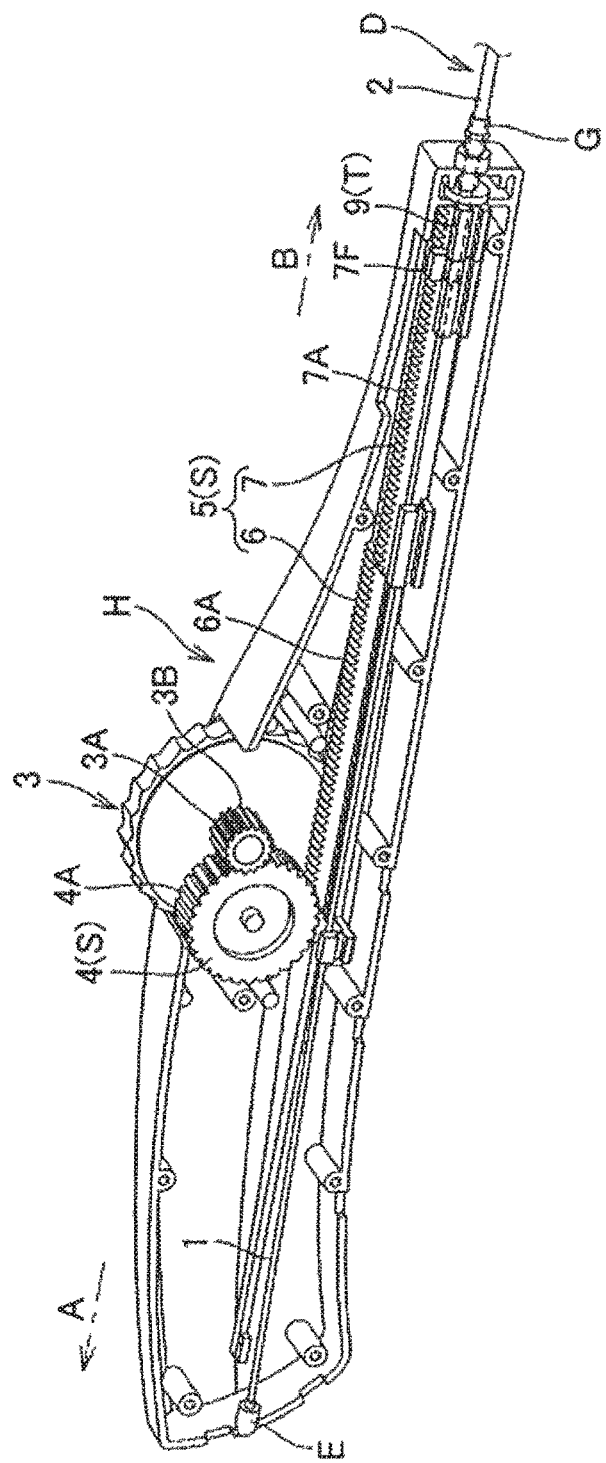
[Fig. 7]

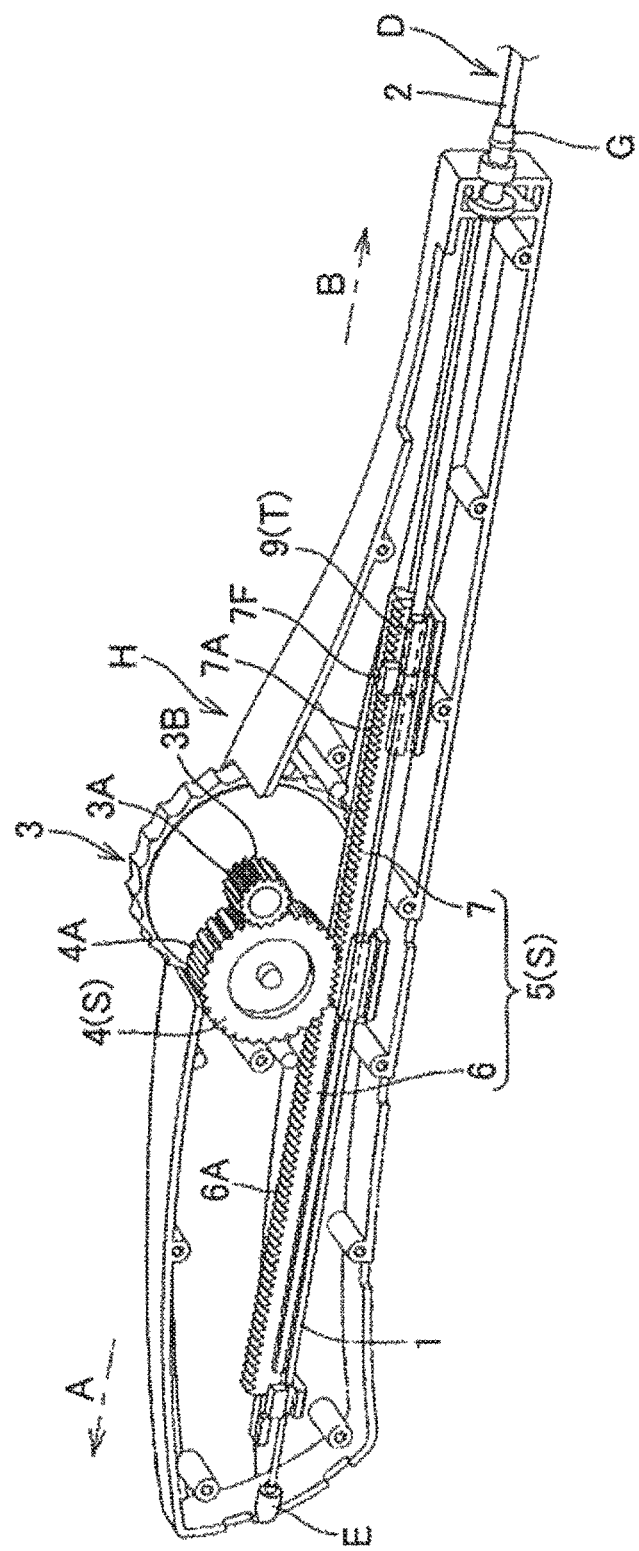
[Fig. 8]

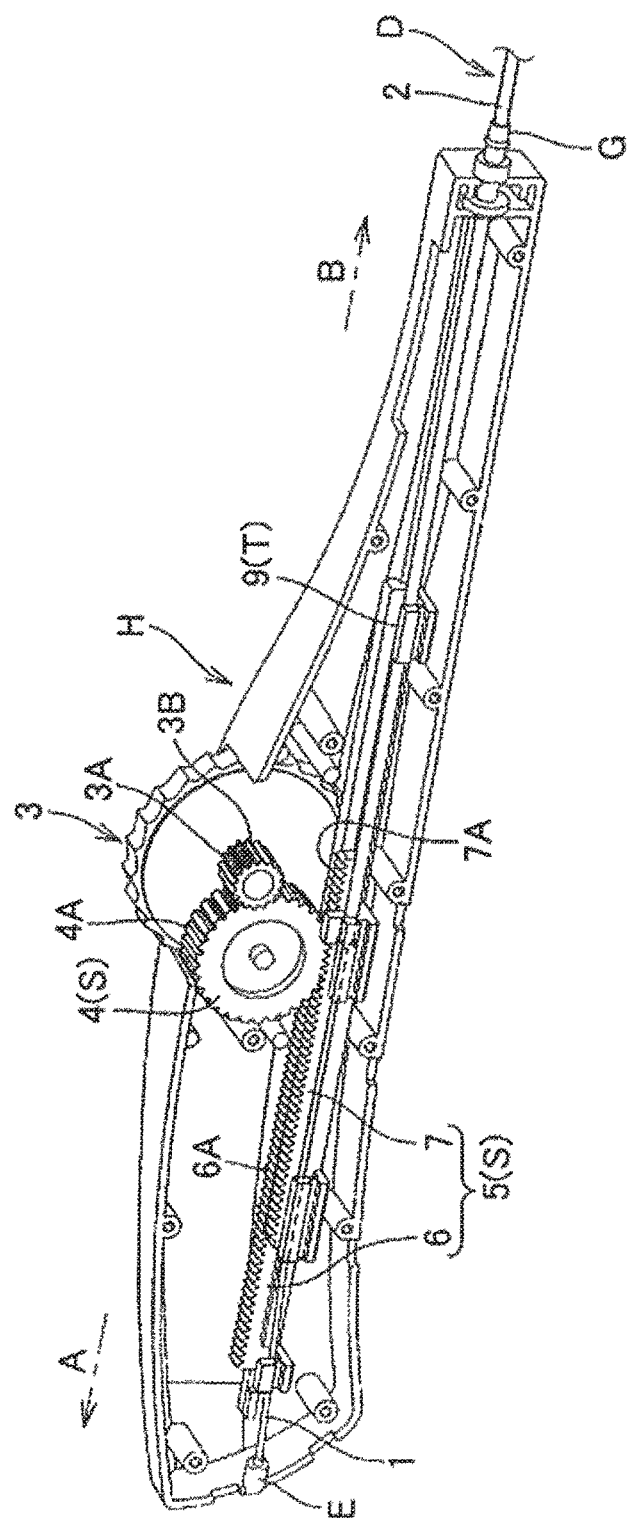
[Fig. 9]

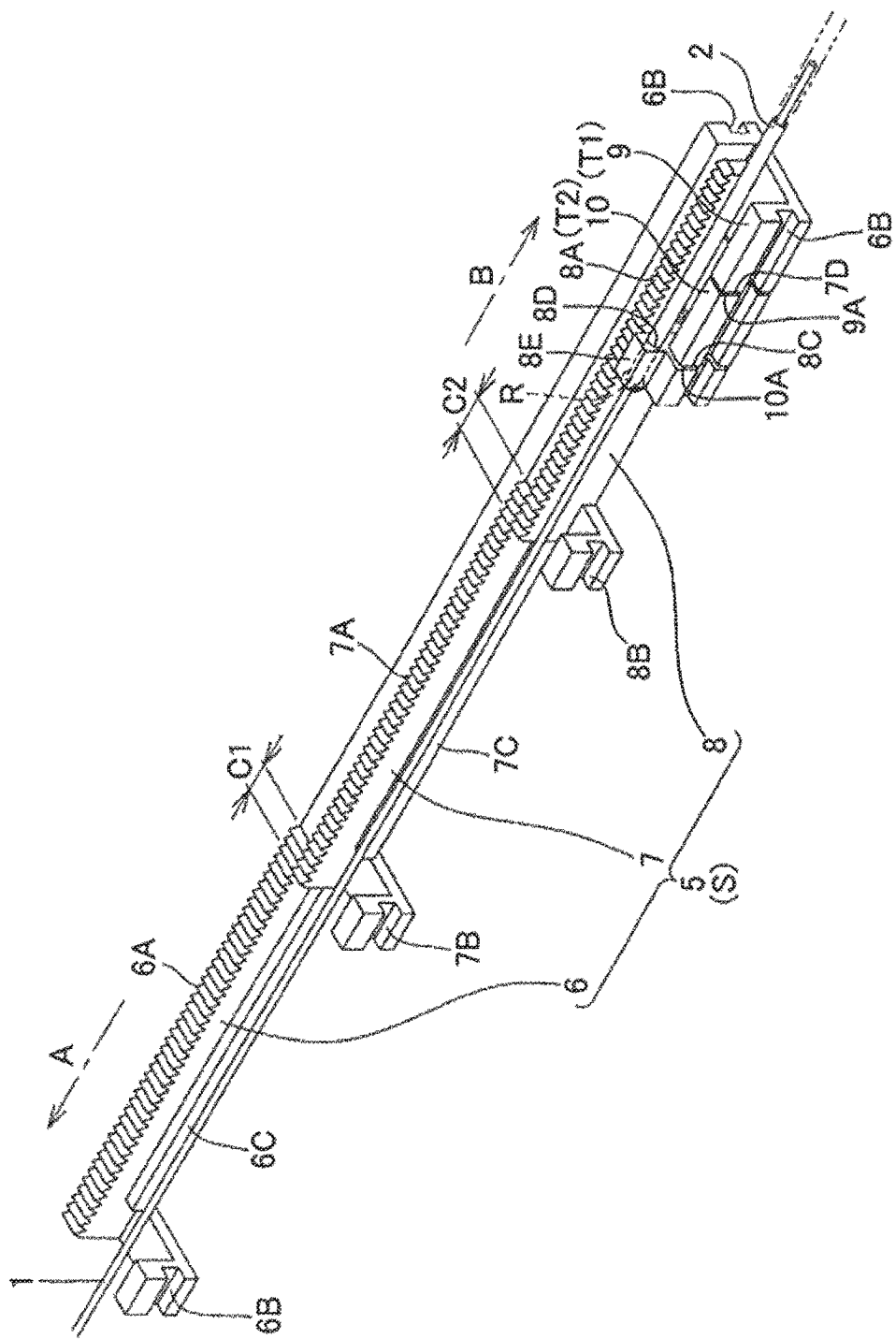
[Fig. 10]

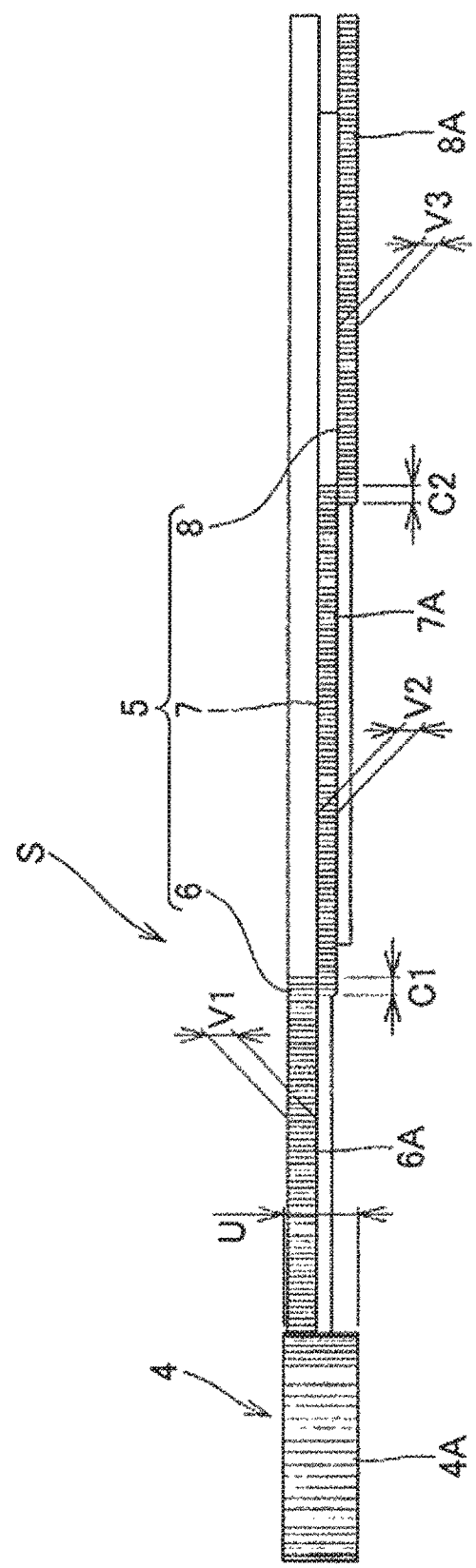
[Fig. 11]

OPERATING HANDLE AND STENT DELIVERY SYSTEM

CROSS REFERENCE TO RELATED APPLICATIONS

This application is a Continuation-in-Part of PCT International Application No. PCT/JP2015/071372, filed on Jul. 28, 2015, which claims priority under 35 U.S.C. 119(a) to Patent Application No. 2014-215947, filed in Japan on Oct. 23, 2014, all of which are hereby expressly incorporated by reference into the present application.

TECHNICAL FIELD

The present invention relates to an operating handle for holding a delivery catheter, and to a stent delivery system provided with the operating handle and for delivering a self-expandable stent held by the delivery catheter to an affected part.

BACKGROUND ART

A stent delivery system delivers a self-expandable stent to an affected part (lesioned part) to widen a narrow segment or an occluded part occurred in a lumen, such as a blood vessel, of a patient and to releases and deploys the self-expandable stent at a position where the stent is delivered. The stent delivery system includes a delivery catheter configured to include coaxial inner and outer shafts, a self-expandable stent held on a distal part of the delivery catheter in a state in which the stent is reduced in diameter, and an operating handle connected to a proximal part of the delivery catheter (for example, see Patent Literatures 1 to 3, and Non-Patent Literature 1).

Here, the operating handle (for example, "an operating handle 12" in Patent Literature 1, "an operating part 18" in Patent Literature 2, "a controller 10" in Patent Literature 3, and "a handle" in Non-Patent Literature 1) includes a rack and pinion mechanism for linearly converting rotation of a pinion by a rack that engages with the pinion and a thumbwheel for operating the rack and pinion mechanism. The rack and pinion mechanism is configured to include a slide mechanism that moves the outer shaft to a proximal side with respect to the inner shaft during release of the self-expandable stent.

CITATION LIST

Patent Literature

Patent Literature 1

Japanese Unexamined Patent Application Publication No. 2007-504897

Patent Literature 2

Japanese Unexamined Patent Application Publication No. 2012-170469

Patent Literature 3

Japanese Unexamined Patent Application Publication No. 2013-192566

Non Patent Literature

Non Patent Literature 1

An instruction manual of "Epic Biliary Stent" (medical device approval number: 22200BZX00794000), Boston Scientific Japan K. K., revised on Mar. 18, 2014 (3rd Edition) (http://www.bostonscientific.jp/templatedata/imports/collateral/Endoscopy/dfu_Ep ic_en.pdf)

SUMMARY OF INVENTION

Technical Problem

A self-expandable stent needs to be securely positioned to an affected part within an error of several millimeters, and a hand technique of an operator performed by operating an operating handle is basically one-hand operation. Accordingly, it is desired to enhance operability of the operating handle.

Due to a relatively small number of components, secure operation, and a low risk of failure, the rack and pinion mechanism widely used for a conventional operating handle is suitable for a slide mechanism for an operating handle of a stent delivery system that requires high reliability in operation.

However, since the rack and pinion mechanism is configured to linearly convert rotation of a pinion by a rack, it needs twice or more a length of a necessary stroke (a necessary slide length of the slide mechanism). Accordingly, a space occupied by the slide mechanism in the operating handle is large.

Therefore, an entire length of the operating handle held by the operator in his/her hand to perform the hand technique is increased, and a volume and a weight of the operating handle become larger. Accordingly, the operating handle equipped with the rack and pinion mechanism does not fit to the operator's hand, and a size or a weight of the operating handle is not suitable for the operator's operation.

Hence, there is room for improvement in the conventional operating handle in terms of further enhancing operability.

In addition, when the entire length of the operating handle is increased, a length of the inner shaft in a base body of the operating handle is increased. Accordingly, deploying accuracy of the self-expandable stent may be lowered by deflection or buckling of the inner shaft at this part.

In addition to that, a synthetic resin that forms the base body or a component of the operating handle absorbs gas during an EOG (ethylene oxide gas) sterilization process. Accordingly, an increase in the volume of the operating handle may lead to defective sterilization, or may lead to an increase in a remaining risk of highly toxic EOG whose remaining gas can adversely affect a human body or the like.

Further, when the operating handles are stacked within a chamber for the EOG sterilization process, an increase in the weight of the operating handle may cause damage to the operating handle due to a load.

Furthermore, as the volume of the operating handle becomes larger, transportation cost or storage cost increases.

Hence, there is room for improvement in the conventional operating handle in terms of suppressing reduction of the deploying accuracy of the self-expandable stent, in terms of suppressing the defective sterilization of the operating handle, the increase in the remaining risk of the EOG, and the damage caused by stacking the operating handles during the sterilization process, and in terms of reducing the transportation cost and the storage cost.

Therefore, in consideration of the aforementioned situations, the present invention is provided, in an operation handle having a slide mechanism, and a stent delivery system including the operating handle, to enhance operability of the operating handle, to suppress defective sterilization of the operating handle, an increase in a remaining risk of EOG, and damage caused by stacking the operating handles during a sterilization process, and to reduce transportation cost and storage cost, by shortening an entire length of the operating handle.

Solution to Problem

An operation handle according to the present invention, to solve the problem, for holding a delivery catheter including a coaxial inner shaft and an outer shaft, comprises a base body that fixes one of the inner shaft or the outer shaft; and a slide mechanism that holds the other of the inner shaft or the outer shaft and slides the other of those so that a relative position between the inner shaft and the outer shaft is shifted; wherein: the slide mechanism comprises a slide body that slides in a longitudinal direction of the base body; the slide body is configured by a plurality of divided bodies of a $1^{st}$ divided body to a nth divided body, wherein n represents a natural number 2 or more, and the divided bodies are slidable with respect to each other; the divided bodies are configured that the divided body is switched so that a driving force for sliding the slide mechanism is sequentially transmitted from the $1^{st}$ divided body as a most former part to the nth divided body as a most latter part; the other of the inner shaft or the outer shaft is connected to the nth divided body as the most latter part; and a power transmitting means that transmits the driving force of the former part of the divided bodies to the latter part of the divided bodies, while the former part of the divided bodies is slid, to integrally slide the former part and the latter part of the divided bodies, is provided.

According to this configuration, since the slide mechanism that relatively slides the inner shaft and the outer shaft comprises a slide body that is driven by the driving force and slides; the slide body is configured by a plurality of divided bodies, and the divided bodies are slidable with respect to each other; the divided bodies are configured that the divided body is switched so that the driving force is sequentially transmitted from a former part of the divided bodies to a latter part of the divided bodies; and a power transmitting means that transmits the driving force of the former part of the divided bodies to the latter part of the divided bodies, while the former part of the divided bodies is slid, to integrally slide the former part and the latter part of the divided bodies, is provided. The former part of the divided bodies is thus driven, the other of the inner shaft or the outer shaft connected to the most latter part of the divided bodies slides with respect to one of the inner shaft or the outer shaft.

Then, in a state in which the divided bodies are switched so that the latter part of the divided bodies is driven and the former part of the divided bodies is not driven, the former part of the divided bodies is stopped. Accordingly, the former part of the divided bodies is not slid anymore.

Consequently, a length required for the slide mechanism can be shortened, and an entire length of the operating handle can be shortened. This allows to reduce a volume and a weight of the operating handle.

Hence, the entire length of the operating handle held by an operator in his/her hand to perform a hand technique can be shortened, the volume and the weight of the operating handle can be reduced, and operability can be improved.

In addition, since the entire length of the operating handle can be shortened, a length of the inner shaft in the base body of the operating handle is shortened. This allows to prevent deflection or buckling of the inner shaft at this portion, thereby suppressing a decrease in deploying accuracy of the self-expandable stent.

In addition to that, since the volume of the operating handle can be reduced and defective sterilization and an increase in a remaining risk of EOG can be suppressed, efficiency of a sterilization process is enhanced.

Further, since the weight of the operating handle can be reduced, damage to the operating handle due to a load is less likely to occur when the operating handles are stacked within a chamber for the EOG sterilization process.

Furthermore, since the volume of the operating handle can be reduced, transportation cost or storage cost can be reduced.

The operating handle preferably further comprises an operating part connected to the slide body. According to such a configuration, the slide body can be slid to the longitudinal direction of the base body by the operating part.

It is preferred that the operating part is a rotating member and the slide mechanism further comprises a rotating body that rotates in conjunction with a rotation of the rotating member or that is integrated with the rotating member and has a same axis with the rotating member. According to such a configuration, the rotating body provided on the slide mechanism can be rotated by rotating the rotating member, and this allows to easily slide the slide body. Further, the rotating member may be a rotating wheel or a rotating handle.

It is preferred that the plurality of the divided bodies extend in a direction crossing a rotation axis of the rotating body and each of the plurality of the divided bodies is provided with an engaging part that engages with the rotating body.

According to such a configuration, the plurality of divided bodies that configures the slide body extends in the direction crossing the rotation axis of the rotating body, and each of the divided bodies is provided with the engaging part that engages with the rotating body. Consequently, the rotating body that transmits driving force and the plurality of divided bodies, to which a torque of the rotating body is sequentially transmitted, can be configured in a compact and simple manner.

The slide body more preferably has a transition section where the rotating body is engaged with the engaging parts of both the former part and the latter part of the divided bodies, wherein the rotating body is engaged with the engaging part of the latter part of the divided bodies before an engagement between the rotating body and the engaging part of the former part of the divided bodies is released in the transition section.

According to such a configuration, the transition section where the rotating body is engaged with the engaging parts of both the former part and the latter part of the divided bodies is provided when the divided body directly driven by the rotating body is switched from the former part of the divided bodies to the latter part of the divided bodies. Consequently, it is possible to securely prevent occurrence of a defect in which the rotating body is not engaged with the divided body and the slide body does not operate. This improves reliability of the operation of the slide mechanism that includes the rotating body and the slide body configured to include the plurality of divided bodies.

It is even more preferred that the rotating body is a pinion and the engaging part is a tooth of a rack that engages with a tooth of the pinion.

According to such a configuration, the slide mechanism that includes the rotating body and the slide body configured to include the plurality of divided bodies is a rack and pinion mechanism. Consequently, stable and secure operation can be performed by using the rack and pinion mechanism with a relatively small number of components, secure operation, and a low risk of failure. This enhances reliability of the slide mechanism.

A width of the tooth of the pinion is even still more preferably not narrower than a sum width of the tooth of the racks of the plurality of the divided bodies.

According to such a configuration, the tooth of the pinion and the teeth of the racks of the divided bodies directly driven by the pinion are securely engaged.

The operating part is preferably a lever, a slider or a pressing member, and connected to the slide body. The slide body can be easily slid by operating the lever, the slider or the pressing member connected to the slide body.

The power transmitting means is even further more preferably an abutting piece that is provided on the former part of the divided bodies and abuts the latter part of the divided bodies.

According to such a configuration, the power transmitting means transmits the driving force of the former part of the divided bodies to the latter part of the divided bodies, while the former part of the divided bodies is slid, to integrally slide the former part and the latter part of the divided bodies. Since the power transmitting means is configured only by the abutting piece that is provided on the former part of the divided bodies and abuts on the latter part of the divided bodies, the power transmitting means can be realized by a very simple configuration. Consequently, a rise in manufacturing cost can be suppressed, and reliability of operation is enhanced.

A stent delivery system comprises the operating handle, the delivery catheter, and a self-expandable stent held on a distal part of the delivery catheter in a state where the stent is reduced in diameter.

Advantageous Effects of Invention

As described above, an operating handle and a stent delivery system according to the present invention achieve remarkable effects, such as:
(1) an entire length of the operating handle held by an operator in his/her hand to perform a hand technique can be shortened and a volume and a weight of the operating handle can be reduced, thereby improving operability;
(2) since the entire length of the operating handle can be shortened, deflection or buckling of an inner shaft at this portion can be prevented, thereby suppressing a decrease in deploying accuracy of a self-expandable stent;
(3) since the volume of the operating handle can be reduced, efficiency of an EOG sterilization process is enhanced;
(4) since the weight of the operating handle can be reduced, damage to the operating handle due to a load is less likely to occur when the operating handles are stacked within a chamber for the EOG sterilization process; and
(5) since the volume of the operating handle can be reduced, transportation cost or storage cost can be reduced.

BRIEF DESCRIPTION OF THE DRAWINGS

FIG. 1 is a perspective view showing a stent delivery system according to an embodiment of the present invention.

FIGS. 2A and 2B are enlarged perspective views of a main part showing a configuration of a distal part of a delivery catheter, and FIG. 2A shows a state in which a self-expandable stent reduced in diameter is held in the delivery catheter, and FIG. 2B shows a state in which the self-expandable stent released from the delivery catheter is expanded.

FIG. 3 is an exploded perspective view of an operating handle according to the embodiment of the present invention.

FIG. 4 is an exploded perspective view of a $1^{st}$ divided body, a $2^{nd}$ divided body, a shaft supporting plate, and a base body.

FIGS. 5A and 5B are perspective views of the $1^{st}$ divided body and the $2^{nd}$ divided body that configure a slide body, and FIG. 5A shows an initial state in which the slide body is not driven (a state in which only an engaging part of the $1^{st}$ divided body is engaged with a rotating body), and FIG. 5B shows a state in which a thumbwheel is operated to drive the slide body, the $1^{st}$ divided body is stopped after the engagement between the $1^{st}$ divided body and the rotating body is released, and only an engaging part of the $2^{nd}$ divided body is engaged with the rotating body.

FIG. 6 is a schematic plan view showing an example of a width of a tooth of a pinion and widths of teeth of racks.

FIG. 7 is a perspective view for illustrating operation that shows by extracting only a main part of an operating handle, and shows the initial state in which the slide body is not driven.

FIG. 8 is similarly a perspective view for illustrating operation, and shows the state in which the thumbwheel is operated to drive the slide body, the $1^{st}$ divided body is stopped after the engagement between the $1^{st}$ divided body and the rotating body is released, and only the engaging part of the $2^{nd}$ divided body is engaged with the rotating body, and the $2^{nd}$ divided body is slid to a rear side.

FIG. 9 is similarly a perspective view for illustrating operation, and shows a state in which the thumbwheel is further operated and the $2^{nd}$ divided body is further slid to the rear side.

FIG. 10 is a perspective view showing an example of a slide body having a three-part (three-divided) constitution, and shows an initial state in which the slide body is not driven.

FIG. 11 is a schematic plan view showing an example of a width of a tooth of a pinion and widths of teeth of racks.

DESCRIPTION OF EMBODIMENTS

Next, an embodiment of the present invention is described in detail based on the accompanying drawings. However, the present invention is not limited to a mode shown in the accompanying drawings, and includes all embodiments that satisfy requirements described in the claims.

It should be noted that a direction of the operating handle herein is defined, based on a state in which a slide body is placed in a bottom of the operating handle and in which an operator holds the operating handle so that a longitudinal direction of the operating handle is placed in a front and rear direction of the operator. In this state, front, back, right and left of the operator are regarded to be "front, back, right and left" of the operating handle. Further, a rear side seen from the operator (a direction of an arrow A in the drawing) is referred to as "a proximal side" of the operating handle, and a front side seen from the operator (a direction of an arrow B in the drawing) is referred to as "a distal side" of the operating handle.

As shown in the perspective view of FIG. 1, a stent delivery system SDS according to an embodiment of the present invention comprises a delivery catheter D including a coaxial inner shaft 1 and an outer shaft 2, a self-expandable stent ST held on a distal part of the delivery catheter D, and an operating handle H for holding the delivery catheter D.

Here, the self-expandable stent ST is a netlike tube body made of, for example, a nickel titanium alloy as a superelastic alloy, and, as shown in an enlarged perspective view of a main part in FIG. 2A, is held by a distal part of the delivery catheter D in a reduced diameter state.

A distal tip F in the enlarged perspective view of the main part in FIG. 2 is formed of a soft material in a tapered shape so that the distal tip F does not damage a vascular wall when the delivery catheter D is delivered to an affected part (a lesioned part).

Further, as shown in FIG. 2A, movement of the self-expandable stent ST reduced in diameter to the proximal side is regulated by a pushing member P fixed to the inner shaft 1.

Hence, when the operator unlocks a lock member L shown in FIG. 1 in the state in which the self-expandable stent ST is delivered to the affected part, and then, as shown in FIG. 2B, the operator moves the outer shaft 2 to the proximal side with respect to the inner shaft 1 (see an arrow in FIG. 2A) by operating a thumbwheel 3, for example, the self-expandable stent ST is released from the delivery catheter D and expanded in a radial direction.

Next, a constitution of the operating handle H according to the embodiment of the present invention is described. The operating handle H comprises a base body that fixes one of the inner shaft 1 or the outer shaft 2; and a slide mechanism S that holds the other of the inner shaft 1 or the outer shaft 2 and slides the other of those so that a relative position between the inner shaft 1 and the outer shaft 2 is shifted. The slide mechanism S at least comprises a slide body 5 that slides in a longitudinal direction of the base body. The operating handle H preferably has the operating part connected to the slide body 5. The slide body 5 can be slid to the longitudinal direction of the base body by the operating part. It is more preferred that the operating part is a rotating member and the slide mechanism S further comprises a rotating body that rotates in conjunction with a rotation of the rotating wheel or that is integrated with the rotating wheel and has a same axis with the rotating wheel. Thus, the rotating body provided on the slide mechanism S can be rotated by rotating the rotating member, and this allows to easily slide the slide body. The rotating member may be a rotating wheel or a rotating handle. The constitution of the operating handle H by using an example in which the operating part is the rotating wheel as the rotating member connected to the slide body 5 (the slide mechanism 5), and in which the slide mechanism S is configured by the slide body 5 and the rotating body that rotates in conjunction with a rotation of the rotating member is described below, the present invention is not limited to this embodiment.

As shown in exploded perspective views in FIG. 3 and FIG. 4, a shaft supporting plate K is attached to a base body I by engaging engagement protrusion parts 12A and 12A of the shaft supporting plate K with engagement recess parts 12B and 12B of the base body I. The base bodies I and J are integrated by engaging engagement recess parts 13B, 13B, . . . of the base body I with engagement protrusion parts 13A, 13A, . . . of the base body J.

The thumbwheel 3, as the rotating wheel, is axially supported by a rotation axis M1 of the base body I and a rotation axis M2 of the shaft supporting plate K. Accordingly, the thumbwheel 3 is rotatably supported around the right and left axes, and rotates only in one direction in which an upper side surface of the thumbwheel 3 is moved to the rear side (the proximal side A) by a ratchet mechanism (not shown).

Further, since a rotation axis N of a pinion 4 as a rotating body is supported by a bearing O of the shaft supporting plate K, the pinion 4 is rotatably supported around the right and left axes.

Here, the rotation axis N of the pinion 4 is parallel to the rotation axis of the thumbwheel 3, and a tooth 4A of the pinion 4 engages with a tooth 3B of a gear part 3A that has the same axis as the rotation axis of the thumbwheel 3 and is integrally formed with the thumbwheel 3.

It should be noted that another gear or gear train may be interposed between the pinion 4 and the thumbwheel 3. Further, the gear part 3A of the thumbwheel 3 may be a pinion as the rotating body. (a pinion that engages with teeth 6A, 7A of racks). When the gear part 3A is configured in this way, the gear part 3A becomes a rotating body integrated with the thumbwheel 3 as the rotating wheel and coaxial with the thumbwheel 3.

A slide body 5 is configured by a $1^{st}$ divided body 6 and a $2^{nd}$ divided body 7 which extend in a direction crossing the rotation axis N of the pinion 4. For example, like the present embodiment, the slide body 5 includes the $1^{st}$ divided body 6 and the $2^{nd}$ divided body 7 provided side by side in a direction parallel to the rotation axis N.

Since a protrusion 11A of the base body I and a protrusion 11B of the base body J are engaged with right and left recesses 6B, 6B, . . . , the $1^{st}$ divided body 6 on a left side is supported by the base bodies I and J so as to be slidable in the front and rear direction.

Further, since a protrusion 6C of the $1^{st}$ divided body 6 and the protrusion 11B of the base body J are engaged with right and left recesses 7B, 7B, . . . , the $2^{nd}$ divided body 7 on a right side is supported by the $1^{st}$ divided body 6 and the base body J so as to be slidable in the front and rear direction.

A $1^{st}$ engaging part engaged with the pinion 4, that is, the tooth 6A of the rack that engages with the tooth 4A of the pinion 4, is formed on an upper surface of a rear side part of the $1^{st}$ divided body 6. A $2^{nd}$ engaging part engaged with the pinion 4, that is, the tooth 7A of the rack that engages with the tooth 4A of the pinion 4, is formed on an upper surface of the $2^{nd}$ divided body 7.

Also, the tooth 6A of the rack of the $1^{st}$ divided body 6 engages with the tooth 4A of the pinion 4 in an initial state (a state in which only the engaging part of the $1^{st}$ divided body is engaged with the rotating body). The tooth 7A of the rack of the $2^{nd}$ divided body 7 does not engage with the tooth 4A of the pinion 4 in the initial state, and engages with the tooth 4A of the pinion 4 at a position where the tooth 4A of the pinion 4 does not engage with the tooth 6A of the rack of the $1^{st}$ divided body 6.

Here, as shown in a schematic plan view of FIG. 6, a width U of the tooth 4A of the pinion 4 is not narrower than a sum of a width V1 of the tooth 6A of the rack of the $1^{st}$ divided body 6 and a width V2 of the tooth 7A of the rack of the $2^{nd}$ divided body 7, that is, $U \geq (V1+V2)$.

It is more preferred that $U \geq (V1+V2)$ in terms of securing the engagement between the tooth 4A of the pinion 4 and the teeth 6A, 7A of the racks of the divided bodies 6 and 7 directly driven by the pinion 4. However, if the tooth 4A of the pinion 4 can engage with the teeth 6A and 7A of the racks of the divided bodies 6 and 7 to perform required slide operation, it is possible that $U < (V1+V2)$.

A proximal part of the delivery catheter D is introduced into the base body I and J through a distal receiving member G fixed to a front end parts of the base body I and J.

A proximal part 1A of the inner shaft 1 is connected to a fixing part E of the rear end part of the base body I.

In addition, the proximal part 2A of the outer shaft 2 is fixed to a ring-like member R after inserting into an inserting hole 7E of the $2^{nd}$ divided body 7 and connected to a lower side of a locked part 7F of the $2^{nd}$ divided body 7 as shown in the perspective view of FIG. 5.

In a state in which a leg part of a lock member L in FIG. 3 is inserted into an inserting opening Q of the base body J, since the leg part of the lock member L is abutted on a rear surface of the locked part 7F projecting upward from the front end part of the $2^{nd}$ divided body 7, the sliding of the $2^{nd}$ divided body 7 to the rear side is regulated.

Therefore, in a state in which the sliding of the $2^{nd}$ divided body 7 to the rear side is regulated by a configuration of a power transmitting means T, which will be described below, sliding of the $1^{st}$ divided body 6 to the rear side is also regulated. Hence, the pinion 4 engaged with the $1^{st}$ divided body 6 and the thumbwheel 3 engaged with the pinion 4 cannot be rotated and are held in a locked state.

When the operator operates the thumbwheel 3 of the operating handle H to move the thumbwheel 3 to the rear side (the proximal side A) in a state in which the lock member L shown in FIG. 1 and FIG. 3 is unlocked, the pinion 4 that engages with the tooth 3B of the gear part 3A rotates in a reverse direction in conjunction with the rotation of the thumbwheel 3. Accordingly, since the slide body 5 slides to the rear side, the outer shaft 2 with the proximal part 2A connected to the $2^{nd}$ divided body 7 is moved to the rear side with respect to the inner shaft 1.

The operating handle H comprises a slide mechanism that slides the outer shaft 2 to the proximal side with respect to the inner shaft 1 when the self-expandable stent ST is sent, and a thumbwheel 3 that operates the slide mechanism S, wherein the slide mechanism S comprises a pinion 4 that is rotating body and rotates in conjunction with a rotation of the thumbwheel 3, and a slide body 5 (the $1^{st}$ divided body 6 and the $2^{nd}$ divided body 7) that is driven by torque of the pinion 4 and slides in a longitudinal direction of the operating handle H.

Next, description is given of a configuration example of the power transmitting means T that transmits a driving force of the $1^{st}$ divided body 6 to the $2^{nd}$ divided body 7, while the $1^{st}$ divided body 6 is slid to the rear side, to integrally slide the $1^{st}$ divided body 6 and the $2^{nd}$ divided body 7.

In an initial state shown in perspective views of FIG. 5A and FIG. 7, the tooth 6A of the rack of the $1^{st}$ divided body 6 engages with the tooth 4A of the pinion 4. When the thumbwheel 3 is moved to the rear side (the proximal side A), the $1^{st}$ divided body 6 is directly driven by the pinion 4 and slid to the rear side.

At this time, an abutting piece 9 that protrudes to a right side is provided in a front end part of the $1^{st}$ divided body 6, and a distal side surface (a front surface) 7D of the $2^{nd}$ divided body 7 (see also FIG. 5B) abuts on a proximal side surface (a rear surface) 9A of the abutting piece 9. Accordingly, the $2^{nd}$ divided body 7 is indirectly driven by the thumbwheel 3 and the pinion 4 via the $1^{st}$ divided body 6, and is slid to the rear side together with the $1^{st}$ divided body 6.

When the power transmitting means T comprises the abutting piece 9 that abuts on the distal side surface 7D of the $2^{nd}$ divided body 7 provided on the $1^{st}$ divided body 6 in this manner, the power transmitting means T can be realized with a very simple constitution. This allows to suppress a rise in manufacturing cost and to increase reliability of operation.

Next, operation of the slide mechanism S based on the operation of the thumbwheel 3 of the operating handle H is described in detail.

When the lock member L is unlocked in the perspective view of FIG. 1 and the thumbwheel 3 is moved to the rear side (the proximal side A) in the initial state shown in the perspective views of FIG. 5A and FIG. 7, the pinion 4 in conjunction with the thumbwheel 3 rotates, and the $1^{st}$ divided body 6 having the tooth 6A of the rack that engages with the tooth 4A of the pinion 4 is slid to the rear side. Further, since the $2^{nd}$ divided body 7 is also slid to the rear side together with the $1^{st}$ divided body 6 by the power transmitting means T (the abutting piece 9), the outer shaft 2 connected to the $2^{nd}$ divided body 7 is moved to the rear side.

At a position shown in the perspective view of FIG. 8, that is, a position at which the tooth 6A of the rack of the $1^{st}$ divided body 6 does not engage with the tooth 4A of the pinion 4 and the $1^{st}$ divided body 6 is stopped, the tooth 7A of the rack of the $2^{nd}$ divided body 7 engages with the tooth 4A of the pinion 4. When the thumbwheel 3 is further moved to the rear side (the proximal side A), only the $2^{nd}$ divided body 7 is slid to the rear side as shown in the perspective views of FIG. 5B and FIG. 9. As a result, the outer shaft 2 connected to the $2^{nd}$ divided body 7 is moved to the rear side.

In the operation of the slide body 5 (the $1^{st}$ divided body 6 and the $2^{nd}$ divided body 7) of the above-described slide mechanism S, a rear end of the $1^{st}$ divided body 6 in a state in which the $1^{st}$ divided body 6 is stopped shown in FIG. 8 is at the rearmost position of the slide body 5 in the operation of the slide mechanism S. Even when the thumbwheel 3 is further moved to the rear side and the $2^{nd}$ divided body 7 (the outer shaft 2) is slid to the rear side from this state, the rearmost position of the slide body 5 (the rear end position of the $1^{st}$ divided body 6) is not changed as shown in FIG. 9.

In the initial state in FIG. 5A, a part formed with the tooth 6A of the rack as the $1^{st}$ engaging part of the $1^{st}$ divided body 6 and a part formed with the tooth 7A of the rack as the $2^{nd}$ engaging part of the $2^{nd}$ divided body 7 have an overlapping part C that overlaps at positions in the front and rear direction of the parts (see also the schematic plan view in FIG. 6).

Hence, the tooth 4A of the pinion 4 engages with the tooth 7A of the rack of the $2^{nd}$ divided body 7 before the tooth 4A of the pinion 4, as the rotating body, does not engage with the tooth 6A of the rack of the $1^{st}$ divided body 6.

When a transition section (the overlapping part C) where the pinion 4, as the rotating body, is engaged with both the $1^{st}$ divided body 6 and the $2^{nd}$ divided body 7 is provided in this manner, it is possible to securely prevent occurrence of a defect in which the pinion 4, as the rotating body, is not engaged with the divided body and the slide body 5 does not operate. This improves reliability of the operation of the slide mechanism S.

It should be noted that, if the transition section (the overlapping part C) is eliminated and a clearance is provided between a front end of the tooth 6A of the rack and a rear end of the tooth 7A of the rack, torque of the pinion 4, as the rotating body, is not transmitted to the slide body 5. Accordingly, the slide body 5 does not operate, thereby becoming inoperative.

Further, in a case where the transition section (the overlapping part C) is eliminated and a clearance is not provided between the front end of the tooth 6A of the rack and the rear end of the tooth 7A of the rack, that is, a case where positions in the front and rear direction of the front end of the tooth 6A of the rack and the rear end of the tooth 7A of the rack are the same, the slide body 5 does not become inoperative. However, considering a variation in shape accuracy of components, assembling accuracy thereof, or the like, the transition section (the overlapping part C) is preferably provided to further enhance reliability of the operation.

The above description has shown a case where the slide body 5 has the two-part (two-divided) constitution formed with the $1^{st}$ divided body 6 as a former part and the $2^{nd}$ divided body 7 as a latter part. Since the slide body 5 has the two-part (two-divided) constitution, while an increase in the manufacturing cost is suppressed by the small number of parts and the simple configuration, an entire length of the operating handle H can be shortened by shortening the length required for the slide mechanism S.

For example, when a necessary stroke (a necessary slide length of a slide mechanism) is 150 mm, the entire length of the operating handle H is about 340 mm in the operating handle H using the conventional rack and pinion mechanism in which the slide body is not divided. However, in the design example of the present invention in which the slide body 5 has the two-part (two-divided) constitution, the entire length of the operating handle H can be about 240 mm.

The slide body 5 may comprise divided bodies of three parts (three divisions) or more. An example of the slide body 5 having a three-part (three-divided) constitution is shown in the perspective view of FIG. 10.

It should be noted that FIG. 10 shows an initial state in which the slide body 5 is not driven and that identical reference signs as those in FIG. 5 denote identical or corresponding parts.

A slide body 5 is configured by a $1^{st}$ divided body 6, a $2^{nd}$ divided body 7 and a $3^{rd}$ divided body 8 which extend in a direction crossing the rotation axis N (see FIG. 3) of the pinion 4. For example, like the embodiment of FIG. 10, the slide body 5 includes the $1^{st}$ divided body 6, the $2^{nd}$ divided body 7 and the $3^{rd}$ divided body 8 provided side by side in a direction parallel to the rotation axis N.

Since a protrusion 7C of the $2^{nd}$ divided body 7 and a protrusion 11B of the base body J are engaged with right and left recesses 8B, 8B, . . . , a $3^{rd}$ slide body 8 is supported by the $2^{nd}$ divided body 7 and the base body J so as to be slidable in the front and rear direction.

Further, the proximal part 2A of the outer shaft 2 is fixed to a ring-like member R after inserting into an inserting hole 8D of the $3^{rd}$ divided body 8 and connected to a lower side of a locked part 8E of the $3^{rd}$ divided body 8.

In the slide body 5 of FIG. 10, a $1^{st}$ engaging part engaged with the pinion 4, that is, the tooth 6A of the rack that engages with the tooth 4A of the pinion 4, is formed on an upper surface of a rear side part of the $1^{st}$ divided body 6. A $2^{nd}$ engaging part engaged with the pinion 4, that is, the tooth 7A of the rack that engages with the tooth 4A of the pinion 4, is formed on an upper surface of a rear side part of the $2^{nd}$ divided body 7. A $3^{rd}$ engaging part engaged with the pinion 4, that is, the tooth 8A of the rack that engages with the tooth 4A of the pinion 4, is formed on an upper surface of the $3^{rd}$ divided body 8.

Also, the tooth 6A of the rack of the $1^{st}$ divided body 6 engages with the tooth 4A of the pinion 4 in an initial state. The tooth 7A of the rack of the $2^{nd}$ divided body 7 does not engage with the tooth 4A of the pinion 4 in the initial state, and engages with the tooth 4A of the pinion 4 at a position where the tooth 4A of the pinion 4 does not engage with the tooth 6A of the rack of the $1^{st}$ divided body 6. The tooth 8A of the rack of the $3^{rd}$ divided body 8 does not engage with the tooth 4A of the pinion 4 in the initial state, and engages with the tooth 4A of the pinion 4 at a position where the tooth 4A of the pinion 4 does not engage with the tooth 7A of the rack of the $2^{nd}$ divided body 7.

Here, as shown in a schematic plan view of FIG. 11, a width U of the tooth 4A of the pinion 4 is not narrower than a sum of a width V1 of the tooth 6A of the rack of the $1^{st}$ divided body 6, a width V2 of the tooth 7A of the rack of the $2^{nd}$ divided body 7 and a width V3 of the tooth 8A of the rack of the $3^{rd}$ divided body 8, that is, U≥(V1+V2+V3).

It is more preferred that U≥(V1+V2+V3) in terms of securing the engagement between the tooth 4A of the pinion 4 and the teeth 6A, 7A and 8A of the racks of the divided bodies 6, 7 and 8 directly driven by the pinion 4. However, if the tooth 4A of the pinion 4 can engage with the teeth 6A, 7A and 8A of the racks of the divided bodies 6, 7 and 8 to perform required slide operation, it is possible that U<(V1+V2+V3).

Next, description is given of a configuration example of the power transmitting means T1 and T2. T1 transmits a driving force of the $1^{st}$ divided body 6 to the $2^{nd}$ divided body 7 and the $3^{rd}$ divided body 8, while the $1^{st}$ divided body 6 is slid to the rear side, to integrally slide the $1^{st}$ divided body 6, the $2^{nd}$ divided body 7 and the $3^{rd}$ divided body 8. T2 transmits a driving force of the $2^{nd}$ divided body 7 to the $3^{rd}$ divided body 8, while the $1^{st}$ divided body 6 is stopped and the $2^{nd}$ divided body 7 is slid to the rear side, to integrally slide the $2^{nd}$ divided body 7 and the $3^{rd}$ divided body 8.

In an initial state shown of FIG. 10, the tooth 6A of the rack of the $1^{st}$ divided body 6 engages with the tooth 4A of the pinion 4. Accordingly, when the thumbwheel 3 is moved to the rear side (the proximal side A), the $1^{st}$ divided body 6 is directly driven by the pinion 4 and slid to the rear side.

At this time, an abutting piece 9 that protrudes to a right side is provided in a front end part of the $1^{st}$ divided body 6, and a distal side surface (a front surface) 7D of the $2^{nd}$ divided body 7 abuts on a proximal side surface (a rear surface) 9A of the abutting piece 9. Accordingly, the $2^{nd}$ divided body 7 is indirectly driven by the same thumbwheel 3 and the pinion 4 as in FIG. 7 via the $1^{st}$ divided body 6, and is slid to the rear side together with the $1^{st}$ divided body 6.

Also, a protruded piece 10 that protrudes to a right side is provided in a front end part of the $2^{nd}$ divided body 7, and a distal side surface (a front surface) 8C of the $3^{rd}$ divided body 8 abuts on a proximal side surface (a rear surface) 10A of an abutting piece 10. Accordingly, the $3^{rd}$ divided body 8 is indirectly driven via the $2^{nd}$ divided body 7, and is slid to the rear side together with the $1^{st}$ divided body 6 and the $2^{nd}$ divided body 7.

The $1^{st}$ divided body 6 is directly driven by the pinion 4 from the initial state shown in FIG. 10 and then the whole slide body 5 moves to the rear side. In a state in which the $1^{st}$ divided body 6 is not driven by the pinion 4 and the $1^{st}$ divided body 6 is stopped, the $2^{nd}$ divided body 7 is directly driven by the pinion 4. In this state, since the distal side surface (the front surface) 8C of the $3^{rd}$ divided body 8 abuts on the proximal side surface (the rear surface) 10A of the abutting piece 10, the $3^{rd}$ divided body 8 moves to the rear side together with the $2^{nd}$ divided body 7.

When the power transmitting means T1 comprises the abutting piece 9 that is provided on the $1^{st}$ divided body 6 and abuts on the distal side surface 7D of the $2^{nd}$ divided body 7 and the power transmitting means T2 comprises the abutting piece 10 that is provided on the $2^{nd}$ divided body 7 and abuts on the distal side surface 8C of the $3^{rd}$ divided body 8 in this manner, the power transmitting means T1 and T2 can be realized with a very simple constitution. This allows to suppress a rise in manufacturing cost and to increase reliability of operation.

Next, operation of the slide body 5 (the $1^{st}$ divided body 6, the $2^{nd}$ divided body 7 and the $3^{rd}$ divided body 8) in FIG. 10 is described.

When the thumbwheel 3 (see FIG. 7) is moved to the rear side (the proximal side A) in the initial state shown in FIG. 10, the pinion 4 in conjunction with the thumbwheel 3 rotates, and the $1^{st}$ divided body 6 having the tooth 6A of the rack that engages with the tooth 4A of the pinion 4 is slid to the rear side. Further, since the $2^{nd}$ divided body 7 and the $3^{rd}$ divided body 8 are also slid to the rear side together with the $1^{st}$ divided body 6 by the power transmitting means T1 (the abutting piece 9), the outer shaft 2 connected to the $3^{rd}$ divided body 8 is moved to the rear side.

Also, at a position at which the tooth 6A of the rack of the $1^{st}$ divided body 6 does not engage with the tooth 4A of the pinion 4 by moving the thumbwheel 3 to the rear side (the proximal side A) and the $1^{st}$ divided body 6 is stopped, the tooth 7A of the rack of the $2^{nd}$ divided body 7 engages with the tooth 4A of the pinion 4. When the thumbwheel 3 is further moved to the rear side (the proximal side A) and the $2^{nd}$ divided body 7 and the $3^{rd}$ divided body 8 are slid to the rear side by the power transmitting means T2 (the abutting piece 10), the outer shaft 2 connected to the $3^{rd}$ divided body 8 is moved to the rear side.

At a position at which the tooth 7A of the rack of the $2^{nd}$ divided body 7 does not engage with the tooth 4A of the pinion 4 by further moving the thumbwheel 3 to the rear side (the proximal side A) and the $2^{nd}$ divided body 7 is stopped, only the $3^{rd}$ divided body 8 is slid to the rear side. As a result, the outer shaft 2 connected to the $3^{rd}$ divided body 8 is moved to the rear side.

In the initial state in FIG. 10, a part formed with the tooth 6A of the rack as the $1^{st}$ engaging part of the $1^{st}$ divided body 6 and a part formed with the tooth 7A of the rack as the $2^{nd}$ engaging part of the $2^{nd}$ divided body 7 have an overlapping part C1 that overlaps at positions in the front and rear direction of the parts (see also the schematic plan view in FIG. 11).

Hence, the tooth 4A of the pinion 4 engages with the tooth 7A of the rack of the $2^{nd}$ divided body 7 before the tooth 4A of the pinion 4, as the rotating body, does not engage with the tooth 6A of the rack of the $1^{st}$ divided body 6.

Also, in the initial state in FIG. 10, a part formed with the tooth 7A of the rack as the $2^{nd}$ engaging part of the $2^{nd}$ divided body 7 and a part formed with the tooth 8A of the rack as the $3^{rd}$ engaging part of the $3^{rd}$ divided body 8 have an overlapping part C2 that overlaps at positions in the front and rear direction of the parts (see also the schematic plan view in FIG. 11).

Hence, the tooth 4A of the pinion 4 engages with the tooth 8A of the rack of the $3^{rd}$ divided body 8 before the tooth 4A of the pinion 4, as the rotating body, does not engage with the tooth 7A of the rack of the $2^{nd}$ divided body 7.

When a transition section (the overlapping part C1) where the pinion 4, as the rotating body, is engaged with both the $1^{st}$ divided body 6 and the $2^{nd}$ divided body 7 and a transition section (the overlapping part C2) where the pinion 4, as the rotating body, is engaged with both the $2^{nd}$ divided body 7 and the $3^{rd}$ divided body 8 are provided in this manner, it is possible to securely prevent occurrence of a defect in which the pinion 4, as the rotating body, is not engaged with the divided body and the slide body 5 does not operate, for the same reason as described above in the case where the slide body has the two-part (two-divided) constitution. This improves reliability of the operation of the slide mechanism S.

Since the slide body 5 has the three-part (three-divided) constitution in FIG. 10, while the relatively simple configuration is maintained, an entire length of the operation handle H can be shorter than that of the operating handle comprising the slide body 4 with the two-part (two-divided) constitution by shortening the length required for the slide mechanism S.

For example, when a necessary stroke (a necessary slide length of a slide mechanism) is 150 mm, the entire length of the operating handle H is about 240 mm in a design example in which the slide body 5 has the two-part (two-divided) constitution. However, in the design example of the present invention in which the slide body 5 has the three-part (three-divided) constitution, the entire length of the operating handle H can be about 210 mm.

The above description shows a configuration in which the rotating body of the slide mechanism S is the pinion 4 and in which the tooth of the rack that engages with the pinion 4 is formed on the divided bodies that configure the slide body 5 of the slide mechanism S and that are long in the front and rear direction. In other words, a case where the slide mechanism S is the rack and pinion mechanism is shown. However, the slide mechanism S is not limited to the rack and pinion mechanism.

For example, the slide mechanism S may have a configuration in which the rotating body of the of the slide mechanism S is a friction roller and in which a driven surface (a rubbed surface) driven by the friction roller is formed on the divided bodies that configure the slide body of the slide mechanism S and are long in the front and rear direction. In other words, the slide mechanism S may be a friction drive mechanism.

However, by using the rack and pinion mechanism for the slide mechanism S, stable and secure operation can be performed by using the rack and pinion mechanism with the relatively small number of components, the secure operation, and the low risk of failure. This enhances reliability of the slide mechanism.

The operating part for operating the slide mechanism S may be a rotating member other than the above-mentioned rotating wheel, for example, a rotating handle. The operating part is preferably a lever, a slider or a pressing member, and connected to the slide body. When the lever, the slider or the pressing member connected to the slide body is operated in this manner, the slide body can be easily slid. A rod member having one end fixed to the base body as a fixing end and the other end as a free end is used as the lever, for example. In that case, the lever and the slide body are preferably connected with each other by a link or a pin. In this manner, when the operator grips the other side of the lever, the lever is rotated at the fixing end as a fulcrum, thereby the slide body can be slid. The slider is a member that moves the slide body by reciprocating. A moving direction of the lever is not limited, and may be directed along the longitudinal direction of the base body, for example. A button or a switch are used as the pressing member. A movement distance or a movement direction of the slide body is may be changed corresponding to a depth or a number of presses of the pressing member. The operating part is may be directly connected to the slide mechanism S (the slide body). Also, the operating part is connected to the slide mechanism S (the slide body) by other member (for example, a pinion as the rotating body).

As described above, the slide body 5 of the present invention may be configured by a plurality of divided bodies. That is, the slide body 5 may be configured by a plurality of divided bodies of a $1^{st}$ divided body to a nth divided body, wherein n represents a natural number 2 or more, and the divided bodies may be slidable with respect to each other.

In this case, the divided bodies are configured that the divided body directly driven by the rotating body is switched so that a torque of the rotating body configuring the slide mechanism S with the slide body 5 is sequentially transmitted from the $1^{st}$ divided body as a most former part to the nth divided body as a most latter part.

Further, the proximal part 1A of the inner shaft 1 is connected to the base body of the operating handle H, and the proximal part 2A of the outer shaft 2 is connected to the nth divided body as the most former part.

Also, the power transmitting means that transmits the driving force of the former part of the divided bodies to the latter part of the divided bodies, while the former part of the divided bodies is slid to the proximal side, to integrally slide the former part and the latter part of the divided bodies, is provided.

According to the configuration of the above-described stent delivery system SDS, when the former part of the divided bodies is driven by the rotating body, the outer shaft 2 with the proximal part 2A connected to the lattermost part of the divided bodies is moved to the proximal side A with respect to the inner shaft 1.

Then, in a state in which the divided bodies are switched so that the rotating body drives the latter part of the divided bodies and the former part of the divided bodies is not driven, the former part of the divided bodies is stopped, and thus the former part of the divided bodies is not slid anymore.

Accordingly, since the length required for the slide mechanism S can be shortened, the entire length of the opening handle H can be shortened. This allows to reduce a volume and a weight of the operating handle H.

Hence, the entire length of the operating handle H held by an operator in his/her hand to perform a hand technique can be shortened and the volume and the weight of the operating handle H can be reduced, thereby improving operability.

Also, since the length of the operating handle H can be shortened, the length of the inner shaft 1 in the base body of the operating handle H is shortened. Thus, deflection or buckling of the inner shaft 1 at this part can be prevented, thereby suppressing a decrease in deploying accuracy of the self-expandable stent ST.

Further, since the volume of the operating handle can be reduced and a defective sterilization and an increase in a remaining risk of EOG are suppressed, efficiency of an EOG sterilization process is enhanced.

Furthermore, since the weight of the operating handle H can be reduced, damage to the operating handle H due to a load is less likely to occur when the operating handles H are stacked within a chamber for the EOG sterilization process.

Also, since the volume of the operating handle can be reduced, transportation cost or storage cost can be reduced.

Moreover, the plurality of divided bodies that configures the slide body S is disposed side by side in the direction parallel to the rotation axis of the rotating body, and the engaging part engaged with the rotating body is formed on each of the divided bodies. Accordingly, the rotating body that transmits the driving force and the plurality of divided bodies, to which the torque of the rotating body is sequentially transmitted, can be configured in a compact and simple manner.

The above description shows a case where the outer shaft 2 is moved to the proximal side A with respect to the inner shaft 1 by operating the thumbwheel 3 as the rotating wheel of the operating handle H. However, the outer shaft 2 may be fixed to the base body and the inner shaft 1 may be moved to the distal side B. That is, one of the inner shaft 1 or the outer shaft 2 is fixed to the base body of the operating handle H, and the other of the inner shaft 1 or the outer shaft 2 may be slid by the slide mechanism S so that a relative position between the inner shaft 1 and the outer shaft 2 is shifted.

REFERENCE SIGNS LIST

1: an inner shaft
1A: a proximal part
2: an outer shaft
2A: a proximal part
3: a thumbwheel (a rotating wheel)
3A: a gear part
3B: a tooth
4: a pinion (a rotating body)
4A: a tooth
5: a slide body
6: a $1^{st}$ divided body
6A: a tooth of a rack (a $1^{st}$ engaging part)
6B: a recess
6C: a protrusion
7: a $2^{nd}$ divided body
7A: a tooth of a rack (a $2^{nd}$ engaging part)
7B: a recess
7C: a protrusion
7D: a distal side surface
7E: an inserting hole
7F: a locked part
8: a $3^{rd}$ divided body
8A: a tooth of a rack (a $3^{rd}$ engaging part)
8B: a recess
8C: a distal side surface
8D: an inserting hole
8E: a locked part
9 and 10: an abutting piece
9A and 10A: a proximal side surface
11A and 11B: a protrusion
12A: an engagement protrusion part
12B: an engagement recess part
13A: an engagement protrusion part
13B: an engagement recess part
A: a proximal side
B: a distal side
C, C1 and C2: an overlapping part (a transition section)
D: a delivery catheter
E: a fixing part
F: a distal tip
G: a distal receiving member
H: an operating handle
I and J: a base body
K: a shaft supporting plate
L: a lock member
M1, M2 and N: a rotation axis
O: a bearing
P: a pushing member
Q: an inserting opening
R: a ring-like member S: a slide mechanism
SDS: a stent delivery system
ST: a self-expandable stent
T, T1 and T2: a power transmitting means
U: a width of a tooth of a pinion
V1, V2 and V3: a width of a tooth of a rack

The invention claimed is:

1. An operating handle for holding a delivery catheter including a coaxial inner shaft and an outer shaft, comprising:
   a base body that fixes one of the inner shaft or the outer shaft; and
   a slide mechanism that holds the other of the inner shaft or the outer shaft and that slides the other of said inner shaft or outer shaft being held by the slide mechanism so that a relative position between the inner shaft and the outer shaft is shifted;
   wherein:
   the slide mechanism comprises a slide body that slides in a longitudinal direction of the base body;
   the slide body is configured by a plurality of divided bodies of a 1st divided body to a nth divided body, wherein n represents a natural number 2 or more, and the divided bodies are slidable with respect to each other;
   the divided bodies are configured that the divided body is switched so that a driving force for sliding the slide mechanism is sequentially transmitted from the 1st divided body as a most former part to the nth divided body as a most latter part;
   the other of the inner shaft or the outer shaft is connected to the nth divided body as the most latter part; and
   a power transmitter that transmits the driving force of the former part of the divided bodies to the latter part of the divided bodies, while the former part of the divided bodies is slid, to integrally slide the former part and the latter part of the divided bodies, is provided.

2. The operating handle according to claim 1, further comprising an operating part connected to the slide body.

3. The operating handle according to claim 2, wherein the operating part is a rotating member, and the slide mechanism further comprises a rotating body that rotates in conjunction with a rotation of the rotating member or that is integrated with the rotating member and has a same axis with the rotating member.

4. The operating handle according to claim 3, wherein the rotating member is a rotating wheel or a rotating handle.

5. The operating handle according to claim 3, wherein the plurality of the divided bodies extend in a direction crossing a rotation axis of the rotating body, and each of the plurality of the divided bodies is provided with an engaging part that engages with the rotating body.

6. The operating handle according to claim 3, wherein the slide body has a transition section where the rotating body is engaged with the engaging parts of both the former part and the latter part of the divided bodies, wherein the rotating body is engaged with the engaging part of the latter part of the divided bodies before an engagement between the rotating body and the engaging part of the former part of the divided bodies is released in the transition section.

7. The operating handle according to claim 3, wherein the rotating body is a pinion and the engaging part is a tooth of a rack that engages with a tooth of the pinion.

8. The operating handle according to claim 7, wherein a width of the tooth of the pinion is not narrower than a sum width of the tooth of the racks of the plurality of the divided bodies.

9. The operating handle according to claim 2, wherein the operating part is a lever, a slider or a pressing member, and connected to the slide body.

10. The operating handle according to claim 1, wherein the power transmitter is an abutting piece that is provided on the former part of the divided bodies and abuts the latter part of the divided bodies.

11. A stent delivery system comprising:
    the operating handle according to claim 1;
    a delivery catheter; and
    a self-expandable stent held on a distal part of the delivery catheter in a state where the stent is reduced in diameter.

* * * * *